US012262999B2

(12) United States Patent
Govari et al.

(10) Patent No.: US 12,262,999 B2
(45) Date of Patent: *Apr. 1, 2025

(54) USING STATISTICAL CHARACTERISTICS OF MULTIPLE GROUPED ECG SIGNALS TO DETECT INCONSISTENT SIGNALS

(71) Applicant: Biosense Webster (Israel) Ltd., Yokneam (IL)

(72) Inventors: Assaf Govari, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 522 days.

This patent is subject to a terminal disclaimer.

(21) Appl. No.: 16/674,911

(22) Filed: Nov. 5, 2019

(65) Prior Publication Data
US 2021/0127999 A1    May 6, 2021

(51) Int. Cl.
  *A61B 5/28*    (2021.01)
  *A61B 5/00*    (2006.01)
  *A61B 5/283*   (2021.01)
  *G06F 17/18*   (2006.01)

(52) U.S. Cl.
  CPC ............ *A61B 5/283* (2021.01); *A61B 5/6852* (2013.01); *A61B 5/7225* (2013.01); *G06F 17/18* (2013.01)

(58) Field of Classification Search
  CPC .................. A61B 18/1492; A61B 2018/00577
  See application file for complete search history.

(56) References Cited

U.S. PATENT DOCUMENTS

| 8,456,182 B2 | 6/2013 | Bar-Tal et al. |
| 11,366,991 B2 | 6/2022 | Govari et al. |
| 2004/0039293 A1 | 2/2004 | Porath et al. |
| 2016/0089048 A1 | 3/2016 | Brodnick et al. |
| 2017/0251942 A1* | 9/2017 | Brodnick ............. A61B 5/7221 |

(Continued)

FOREIGN PATENT DOCUMENTS

| AU | 2013205728 A1 * 11/2013 ........... A61B 5/7207 |
| EP | 2901953 A1    8/2015 |

(Continued)

OTHER PUBLICATIONS

Roney, Caroline H., et al. "An automated algorithm for determining conduction velocity, wavefront direction and origin of focal cardiac arrhythmias using a multipolar catheter." *2014 36th Annual International Conference of the IEEE Engineering in Medicine and Biology Society.* IEEE, 2014.

(Continued)

*Primary Examiner* — Michael J D'Abreu
(74) *Attorney, Agent, or Firm* — Frost Brown Todd LLP

(57) ABSTRACT

A system includes signal acquisition circuitry and a processor. The signal acquisition circuitry is configured to receive multiple intra-cardiac signals acquired by multiple electrodes of an intra-cardiac probe in a heart of a patient. The processor is configured to extract multiple annotation values from the intra-cardiac signals, to select a group of the intra-cardiac signals, to identify in the group one or more annotation values that are statistically deviant in the group by more than a predefined measure of deviation, and to visualize the annotation values to a user, excluding the statistically deviant annotation values.

5 Claims, 5 Drawing Sheets

(56) References Cited

U.S. PATENT DOCUMENTS

| | | | |
|---|---|---|---|
| 2017/0311833 A1 | 11/2017 | Afonso et al. | |
| 2017/0367603 A1 | 12/2017 | Spector | |
| 2018/0153428 A1* | 6/2018 | Balachandran | ........ A61B 5/367 |
| 2018/0368713 A1 | 12/2018 | Gutbrod et al. | |
| 2019/0030332 A1 | 1/2019 | Ghosh et al. | |
| 2019/0046066 A1 | 2/2019 | Hughes et al. | |
| 2019/0261927 A1* | 8/2019 | Matthiesen | ............ A61B 5/725 |

FOREIGN PATENT DOCUMENTS

| | | |
|---|---|---|
| EP | 3384835 A1 | 10/2018 |
| WO | 2015/031607 A1 | 3/2015 |

OTHER PUBLICATIONS

Yan, Long, et al. "A 13 μA Analog Signal Processing IC for Accurate Recognition of Multiple Intra-Cardiac Signals." *IEEE transactions on biomedical circuits and systems* 7.6 (2013): 785-795.
European Search Report and Written Opinion dated Mar. 24, 2021, for Application No. 20205754.3, 8 pages.
European Communication dated Feb. 28, 2022, for Application No. 20205754.3, 6 pages.
Japanese Notification of Reasons for refusal dated Jun. 4, 2024, for Application No. 2020-184233, 5 pages.

* cited by examiner

USING STATISTICAL CHARACTERISTICS OF MULTIPLE GROUPED ECG SIGNALS TO DETECT INCONSISTENT SIGNALS

CROSS-REFERENCE TO RELATED APPLICATIONS

This application is related to U.S. Patent Application entitled "Optimizing Mapping of ECG Signals Retrospectively by Detecting Inconsistency," U.S. patent application Ser. No. 16/674,921, filed on Nov. 5, 2019, issued as U.S. Pat. No. 11,366,991 on Apr. 21, 2022, whose disclosure is incorporated herein by reference.

FIELD OF THE INVENTION

The present invention relates generally to intrabody medical procedures and instruments, and particularly to intrabody cardiac electrocardiogram (ECG) sensing.

BACKGROUND OF THE INVENTION

When measuring and annotating internal-electrocardiogram (iECG) signals that are generated by a large number of electrodes, it may be desirable to process the signals (e.g., by a computer), in order to reduce the embedded noise.

Various methods exist for such iECG signal processing. For example, US Patent Application Publication 2016/0089048, now issued as U.S. Pat. No. 9,314,179 on Apr. 19, 2026, describes an automatic method of determining local activation time (LAT) of four or more multi-channel cardiac electrogram signals which include a Ventricular channel, a mapping channel and a plurality of reference channels.

Another example is "A 13 µA Analog Signal Processing IC for Accurate Recognition of Multiple Intra-Cardiac Signals", by Yan et al, IEEE Transactions On Biomedical Circuits And Systems, Vol. 7, No. 6, December, 2013, which describes an analog signal processing IC for the low-power heart rhythm analysis, featuring three identical, but independent intra-ECG readout channels, each comprising an analog QRS feature extractor for low-power consumption and fast diagnosis of the electrocardiogram.

SUMMARY OF THE INVENTION

An embodiment of the present invention that is described herein provides a system including signal acquisition circuitry and a processor. The signal acquisition circuitry is configured to receive multiple intra-cardiac signals acquired by multiple electrodes of an intra-cardiac probe in a heart of a patient. The processor is configured to extract multiple annotation values from the intra-cardiac signals, to select a group of the intra-cardiac signals, to identify in the group one or more annotation values that are statistically deviant in the group by more than a predefined measure of deviation, and to visualize the annotation values to a user, excluding the statistically deviant annotation values.

In some embodiments, the processor is configured to define the measure of the deviation in terms of a standard score of the annotation values. In other embodiments, the processor is configured to define the measure of the deviation in terms of one or more percentiles of the annotation values.

In an embodiment, the processor is configured to calculate deviations of the annotation values over intra-cardiac signals acquired by a selected subset of spatially-related electrodes located no more than a predefined distance from one another in the heart. In another embodiment, in calculating deviations of the annotation values, the processor is configured to average the intra-cardiac signals over multiple temporally-related cardiac cycles that occur within a predefined time duration.

In a disclosed embodiment, the processor is configured to correct one or more of the annotation values in a given intra-cardiac signal, acquired by a given electrode in the group, to compensate for a displacement of the given electrode relative to the other electrodes in the group. In some embodiments, the annotation values include Local Activation Times (LATs). In an example embodiment, the processor is configured to visualize the annotation values by overlaying the annotation values, excluding the statistically deviant annotation values, on a model of the heart.

There is additionally provided, in accordance with an embodiment of the present invention, a method including receiving multiple intra-cardiac signals acquired by multiple electrodes of an intra-cardiac probe in a heart of a patient. Multiple annotation values are extracted from the intra-cardiac signals. A group of the intra-cardiac signals is selected. One or more annotation values, which are statistically deviant in the group by more than a predefined measure of deviation, are identified in the group. The annotation values are visualized to a user, excluding the statistically deviant annotation values.

The present invention will be more fully understood from the following detailed description of the embodiments thereof, taken together with the drawings in which:

DETAILED DESCRIPTION OF EMBODIMENTS

Overview

Figure 1:
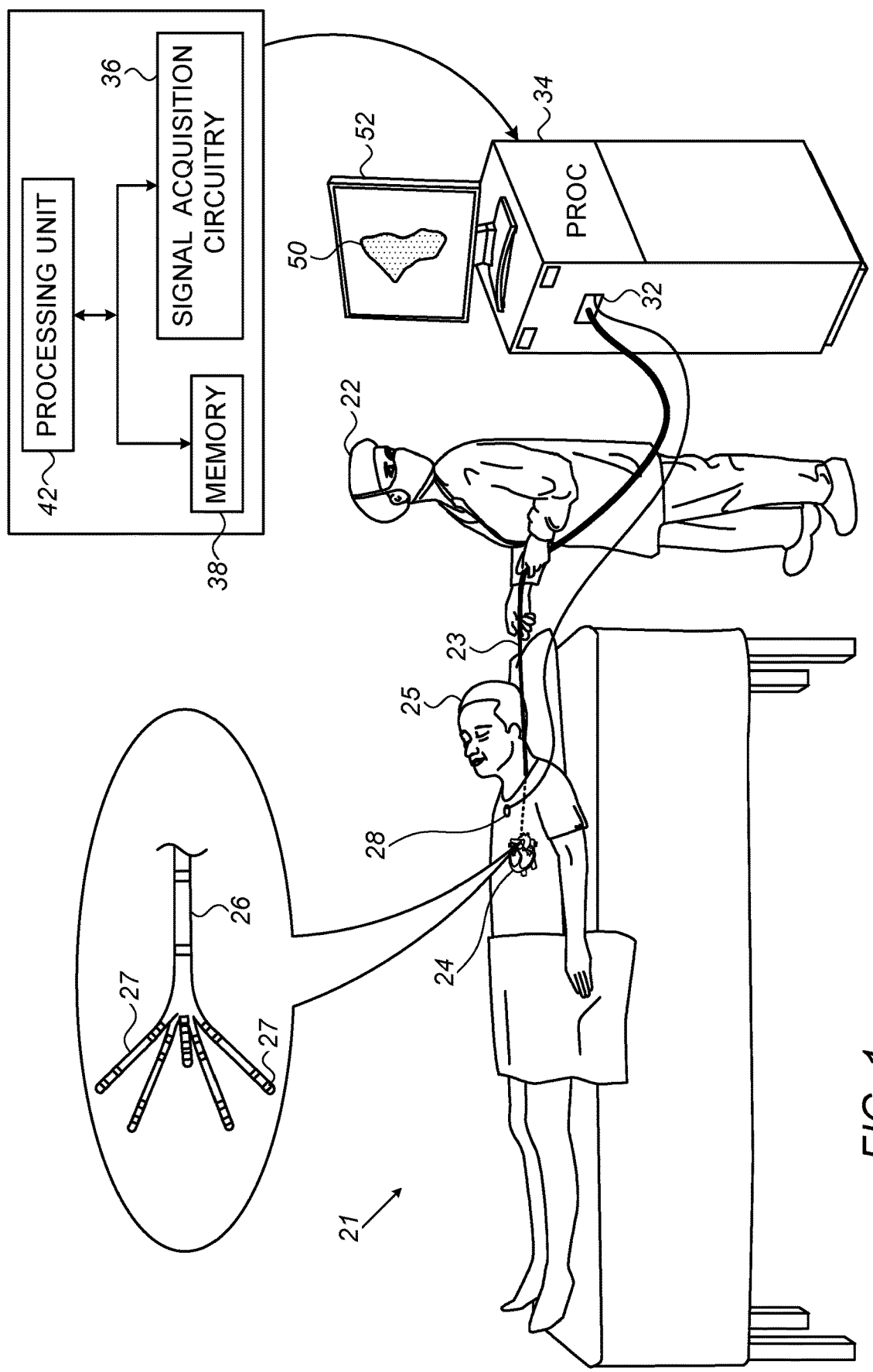
FIG. 1 is a schematic, pictorial illustration of an electroanatomical system for multi-channel measurement of intra-cardiac ECG signals, in accordance with an embodiment of the present invention.

Intra-cardiac probe-based (e.g., catheter-based) cardiac diagnostic and therapeutic systems may measure multiple intra-cardiac signals, such as electrocardiograms (ECG), during an invasive procedure. Such systems may acquire the multiple intra-cardiac signals using electrodes (also referred to hereinafter as "distal electrodes") that are fitted at the distal end of the probe. The measured signals may be used to provide a physician with visual cardiac information such as 3-D mapping of the source of pathological electrical patterns within the heart of the patient, and to support corrective medical procedures such as ablation.

The measured signals are typically weak, with a low Signal to Noise Ratio (SNR). Moreover, the galvanic connection of some of the electrodes with tissue may be poor or non-existent. On the other hand, many electrodes are used, and, hence, there may be some redundancy in the data that the system receives from the electrodes.

Embodiments of the present invention that are disclosed herein provide intra-cardiac probe-based electro-anatomical measurement and analysis systems and methods that use statistical characteristics of the signals that the distal electrodes collect, to improve the quality and reliability of the collected data.

In the description hereinbelow we will refer to annotation value of Local Activation Time (LAT). The disclosed techniques, however, are not limited to LAT; in various embodiments of the present invention, annotation values of various other suitable signal parameters may be used.

In some embodiments according to the present invention, a processor extracts annotation values (e.g., the LAT) of the signals, and then calculates statistical characteristics of the LAT values of a group of signals that are acquired by a corresponding group of electrodes (which may comprise all or some of the electrodes). In an embodiment, the statistical characteristics comprise the mean of the LAT values of the group of signals (e.g., $\bar{x}=\Sigma x/n$); in other embodiments the characteristics further comprise the standard deviation (e.g., $\sigma=\sqrt{(\Sigma(x-\bar{x})^2/n)}$) of the group. The processor then uses statistical methods to determine, for each one of the group of signals, whether annotation values of signals are valid values, or values that should be ignored.

In another embodiment, the statistical characteristics comprise the quartiles of the group of LAT values. The processor calculates the first and the third quartiles $Q1$, $Q3$, and then ignores all values that are lower than $Q1$ or higher than $Q3$ (a first quartile ($Q1$) is defined as the middle number between the smallest number and the median of a data set; a third quartile ($Q3$) is the middle value between the median and the highest value of the data set). Alternatively, the processor may define the measure of deviation of the LAT values in terms of any other suitable percentile (or multiple percentiles) of the LAT values. Further alternatively, any other suitable process that discards outlier LAT values can be used.

The technique disclosed hereinabove assumes that, devoid of noise and irregular galvanic connections, the electrodes of the group exhibit similar annotation values. Typically, the annotation values acquired by electrodes that are remote from each other may vary substantially. In addition, signals from each electrode may be annotated periodically, with each heartbeat ("cardiac cycle"), and annotation values derived from cardiac cycles that are temporally remote from each other may vary. In an embodiment, the group of signals is inter-related. In some embodiments, a tracking system measures the geometrical location of the electrodes, and the group comprises annotation values derived from neighboring electrodes only ("spatially related," i.e., electrodes that are located no more than a predefined distance from one another). In other embodiments the group comprises annotation values derived from neighboring cardiac cycles only ("temporally related," i.e., cardiac cycles that all occur within no more than a predefined time duration); and, in an embodiment, the group comprises values that are both spatially and temporally related (will be referred to, in short, as "related values").

In some embodiments, the processor, after calculating the statistical characteristics of the group of related LAT values, omits LAT values that are statistically deviant in the group, e.g., substantially different from the mean value of the group of values (the group of the remaining LAT values will be referred to as the group of valid LAT values). Thus, LAT values that correspond to poorly connected electrodes, or to electrodes that are subject to extreme noise, may be eliminated from the group of valid LAT values.

In embodiments, to determine whether a LAT value is statistically deviant from the mean LAT of a group of signals, the processor measures the deviation of annotated LAT valued from the mean of the group of LAT values. In an embodiment, the measure of the deviation is the Standard Score of the value (defined as the difference between the value and the mean, divided by the standard deviation), which is compared to preset limits. For example, values that are larger than the mean by more than 3.5 standard deviations (standard score=3.5), or lower than the mean by more than 1.5 standard deviations (standard score=−1.5) may be considered statistically deviant and thus omitted. In another embodiment, the processor omits values that are lower than the first quartile or higher than the third quartile.

In some embodiments of the present invention, the processor may mitigate the variance in LAT values of spatially related electrodes due to the different time delays of cardiac signal propagation within the heart. According to embodiments, the processor may correct the LAT annotation acquired by a given electrode, by compensating for the displacement of the given electrode relative to the other electrodes, so as to cancel the difference in propagation delay.

In summary, according to embodiments of the present invention, the quality and reliability of a group of annotation values of spatially and/or temporally related inter-cardiac signals may be improved by calculating statistical characteristics of the annotation values, comparing the annotation values to the group mean, and omitting from the group of valid values, values that are remote from the mean. In some embodiments, prior to statistical characteristics calculation, the group of annotation values may first be modified to correct for propagation delays of the signals.

System Description

FIG. 1 is a schematic, pictorial illustration of an electro-anatomical system 21 for multi-channel measurement of intra-cardiac ECG signals, in accordance with an embodiment of the present invention. In some embodiments, system 21 is used for electro-anatomical mapping of a heart.

FIG. 1 depicts a physician 22 using an electro-anatomical catheter 23 to perform an electro-anatomical mapping of a heart 24 of a patient 25. Catheter 23 comprises, at its distal end, one or more arms 26, which may be mechanically flexible, to each of which are coupled one or more distal electrodes 27. As would be appreciated, although FIG. 1 depicts a catheter with five arms, other types of catheters may be used in alternative embodiments according to the present invention. The electrodes are coupled, through an interface 32, to a processor 34.

During the electro-anatomical mapping procedure, a tracking system is used to track the intra-cardiac locations of distal electrodes 27, so that each of the acquired electro-physiological signals may be associated with a known intra-cardiac location. An example of tracking system is Active Current Location (ACL), which is described in U.S. Pat. No. 8,456,182. In the ACL system, a processor estimates the respective locations of the distal electrodes based on impedances measured between each of distal electrodes 27 and a plurality of surface electrodes 28 that are coupled to the skin of patient 25. (For ease of illustration, only one surface-electrode is shown in FIG. 1.) The processor may then associate any electrophysiological signal received from distal electrodes 27 with the location at which the signal was acquired.

In some embodiments, multiple distal electrodes 27 acquire intra-cardiac ECG signals from tissue of a cardiac chamber of heart 24. The processor comprises a signal acquisition circuitry 36 that is coupled to receive the intra-cardiac signals from interface 32, a memory 38 to store data and/or instructions, and a processing unit 42 (e.g., a CPU or other processor).

Signal acquisition circuitry 36 digitizes the intra-cardiac signals so as to produce multiple digital signals. The Acquisition Circuitry then conveys the digitized signals to processing unit 42, included in processor 28.

Among other tasks, processing unit 42 is configured to extract annotation parameters from the signals, calculate statistical characteristics such as mean value of the annotated parameters for groups of neighboring signals that are likely to be similar (in the current context, neighboring signals refers to signals from electrodes located close to each other ("spatially related"), and/or to annotation values extracted from cardiac cycles that are close to each other in time ("temporally related")).

The processing unit is further configured, after calculating the statistical characteristics, to drop (i.e., omit) annotation values that are likely to be invalid from the group (such as annotation from electrodes with poor galvanic connection, or subject to an intense temporal noise). The remaining annotation values will be referred to hereinbelow as "valid annotation values."

The processing unit visualizes the valid annotation values, i.e., the annotation values excluding the statistically deviant annotation values that have been omitted, to a user. In some embodiments, processing unit 42 visualizes the valid annotation values, for example, by overlaying them on an electro-anatomical map 50 of the heart and displaying the map to physician 22 on a screen 52. Alternatively, processing unit 42 may visualized the valid annotation values (after omitting the invalid annotation values) in any other suitable way.

The example illustration shown in FIG. 1 is chosen purely for the sake of conceptual clarity. In alternative embodiments of the present invention, for example, position measurements can also be done by applying a voltage gradient between pairs of surface electrodes 28 and measuring, with distal electrodes 27, the resulting potentials (i.e., using the CARTO® 4 technology produced by Biosense-Webster, Irvine, Calif.). Thus, embodiments of the present invention apply to any position sensing method.

Other types of catheters, such as the Lasso® Catheter (produced by Biosense-Webster), or a basket catheter, may equivalently be employed. Contact sensors may be fitted at the distal end of electro-anatomical catheter 23. Other types of electrodes, such as those used for ablation, may be utilized in a similar way on distal electrodes 27 to acquire intra-cardiac electrophysiological signals.

FIG. 1 mainly shows parts relevant to embodiments of the present invention. Other system elements, such as external ECG recording electrodes and their connections are omitted. Various ECG recording system elements are omitted, as well as elements for filtering, digitizing, protecting circuitry, and others.

In an optional embodiment, a read-out application-specific integrated circuit (ASIC) is used for measuring the intra-cardiac ECG signals. The various elements for routing signal acquisition circuitry 36 may be implemented in hardware, e.g., using one or more discrete components, such as field-programmable gate arrays (FPGAs) or ASICs. In some embodiments, some elements of signal acquisition circuitry 36 and/or processing unit 42 may be implemented in software, or by using a combination of software and hardware elements.

Processing unit 42 typically comprises a general-purpose processor with software programmed to carry out the functions described herein. The software may be downloaded in electronic form, over a network, for example, or it may, alternatively or additionally, be provided and/or stored on non-transitory tangible media, such as magnetic, optical, or electronic memory.

Related Annotation Values

Related Annotation Values are derived from spatially related electrodes (e.g., electrodes that are geometrically close to each other, i.e., located no more than a predefined distance from one another) and/or from temporally related signals (e.g., values extracted from cardiac cycles that are close to each other, i.e., occur within no more than a predefined time duration). More precisely, related annotation values are annotation values for which the combined distance, comprising the geometrical distance between the electrodes and the temporal distance between the cardiac cycles, is below some predefined threshold.

Figure 2:
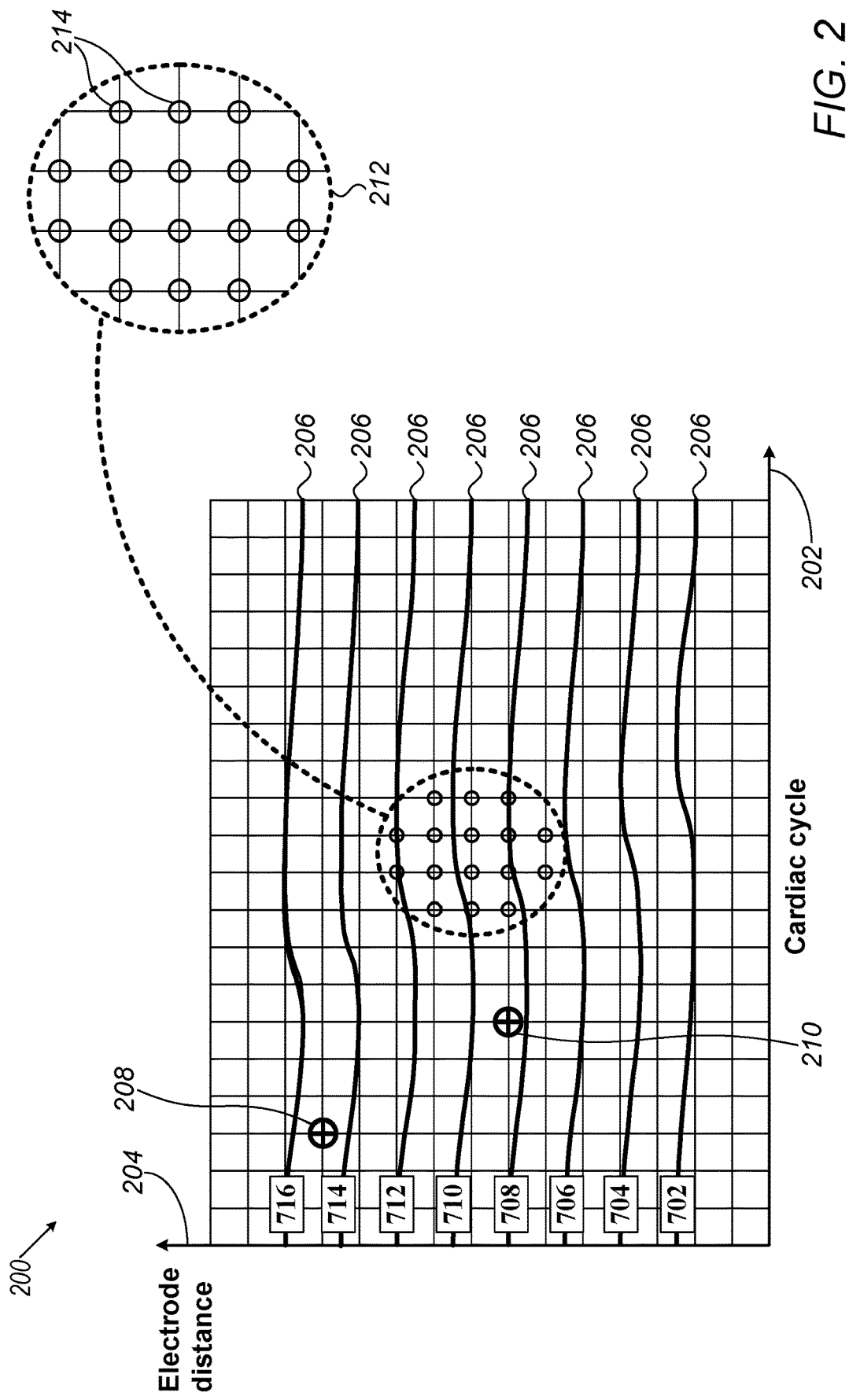
FIG. 2 is a diagram that schematically illustrates acquisition of signals by multiple electrodes at multiple cardiac cycles, in accordance with an embodiment of the present invention.

FIG. 2 is a diagram 200 that schematically illustrates acquisition of signals by multiple electrodes at multiple cardiac cycles. A horizontal axis 202 shows the cardiac cycle (each vertical line is one cardiac cycle), and a vertical axis 204 shows the distance of the electrode from a reference point (only one spatial dimension is shown; as would be appreciated, two or three dimensions may be used in practice, but are not shown, for clarity). According to the example embodiment illustrated in FIG. 2, there are electrodes in all horizontal lines, and LAT annotation values are registered for all intersections of horizontal and vertical lines (each intersection will be referred hereinbelow to as a LAT-point).

Curves 206 are equi-LAT lines, showing the location of the indicated LAT values, and the electrodes are likely to measure, at the corresponding cardiac cycles, values interpolated from the neighboring equi-LAT curves. For example, the expected registered value of LAT-point 208 (which is vertically half-way between equi-LAT lines 714 and 716) is 715, whereas the expected registered value of LAT-point 210 is 708.5.

As can be seen, the LAT values of neighboring vertical lines and of neighboring horizontal lines are similar. Circle 212 represents a group of related LAT values 214, that are close to each other in terms of geometrical (vertical) and temporal (horizontal) distances.

The example illustration shown in FIG. 2 is simplified and shown purely for the sake of conceptual clarity. In alternative embodiments, for example, the distance between the electrodes is not uniform, and, the group of related signals may not be a circle.

Figure 3A:
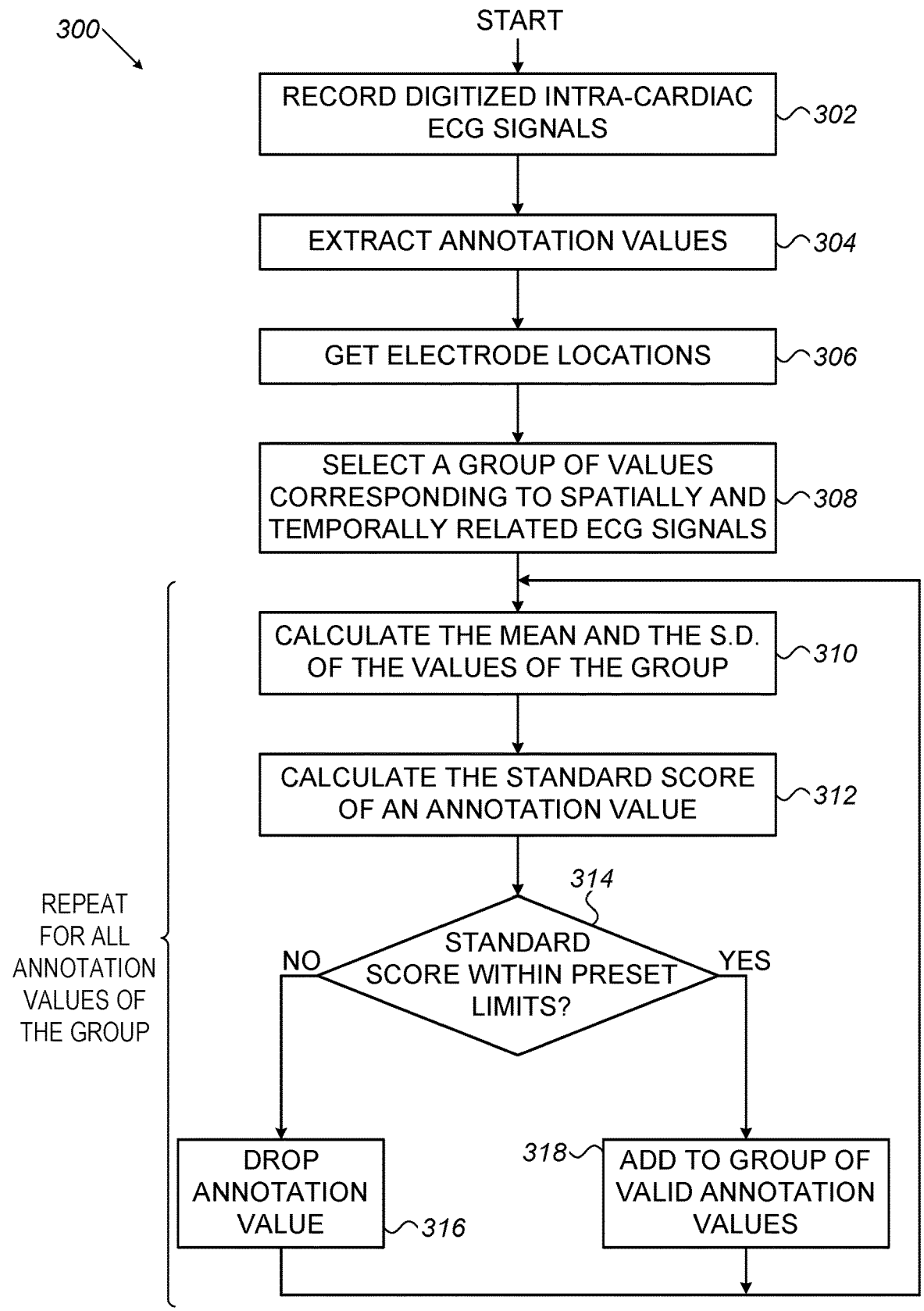
FIG. 3A is a flow chart that schematically illustrates a first method for enhancing the reliability of annotation values, in accordance with an embodiment of the present invention.

FIG. 3A is a flow chart 300 that schematically illustrates a first method for enhancing the reliability of annotation values, according to embodiments of the present invention. The flow is executed by processing unit 42 (FIG. 1). The flow starts at a Recording Signals step 302, wherein the processing unit records ECG signals monitored by electrodes 27 and acquired by acquisition circuitry 36 (FIG. 1). Next, at an Extracting Annotation Values step 304, the processing unit calculates the annotation values for each electrode and each cardiac cycle.

The processing unit then enters a Getting Electrode Location step 306, wherein the location of the electrodes is acquired (e.g., using the ACL technique), and the spatial location of each electrode is registered, and then enters a Selecting Group step 308.

In step 308, the processing unit selects a group of related annotation values. As described hereinabove, the group comprises annotation values that are likely to be similar, from spatially and/or temporally related signals.

Next, in a Calculating Mean and SD step 310, the processing unit calculates the average and standard deviation for all annotation values of the group. In the present context, any suitable type of mean can be used, such as an arithmetic mean, a geometric mean, a median, a Root Mean Square (RMS) value, a center of mass, or any other.

The processing unit then, repeatedly for each annotation value of the group, sequentially enters steps 312, 314, and either step 316 or step 318. In a Calculating Standard Score step 312, the processing unit calculates the standard score of the annotation value (e.g., by dividing the difference between the annotation value and the mean by the standard deviation). In a Comparing Standard Score step 314 the processing unit compares the standard score calculated in step 312 to preset limits. In a Dropping Value step 316, which is entered if the standard score exceeds a preset limit, the processing unit drops the statistically deviant annotation value; and, in an Adding Value step 318, which is entered if the standard score is within the preset limits, the processing unit adds the annotation value to a group of valid annotation values.

The processor repeats the sequence of steps 312, 314 and either step 316 or step 318 for all annotation values of the group. The flow chart may then repeat (from step 308) for other groups of related electrodes.

When the flow ends, groups of valid annotation values replace the original groups, with better reliability, as extreme values (for example, from electrodes with poor galvanic connection) are omitted.

Figure 3B:
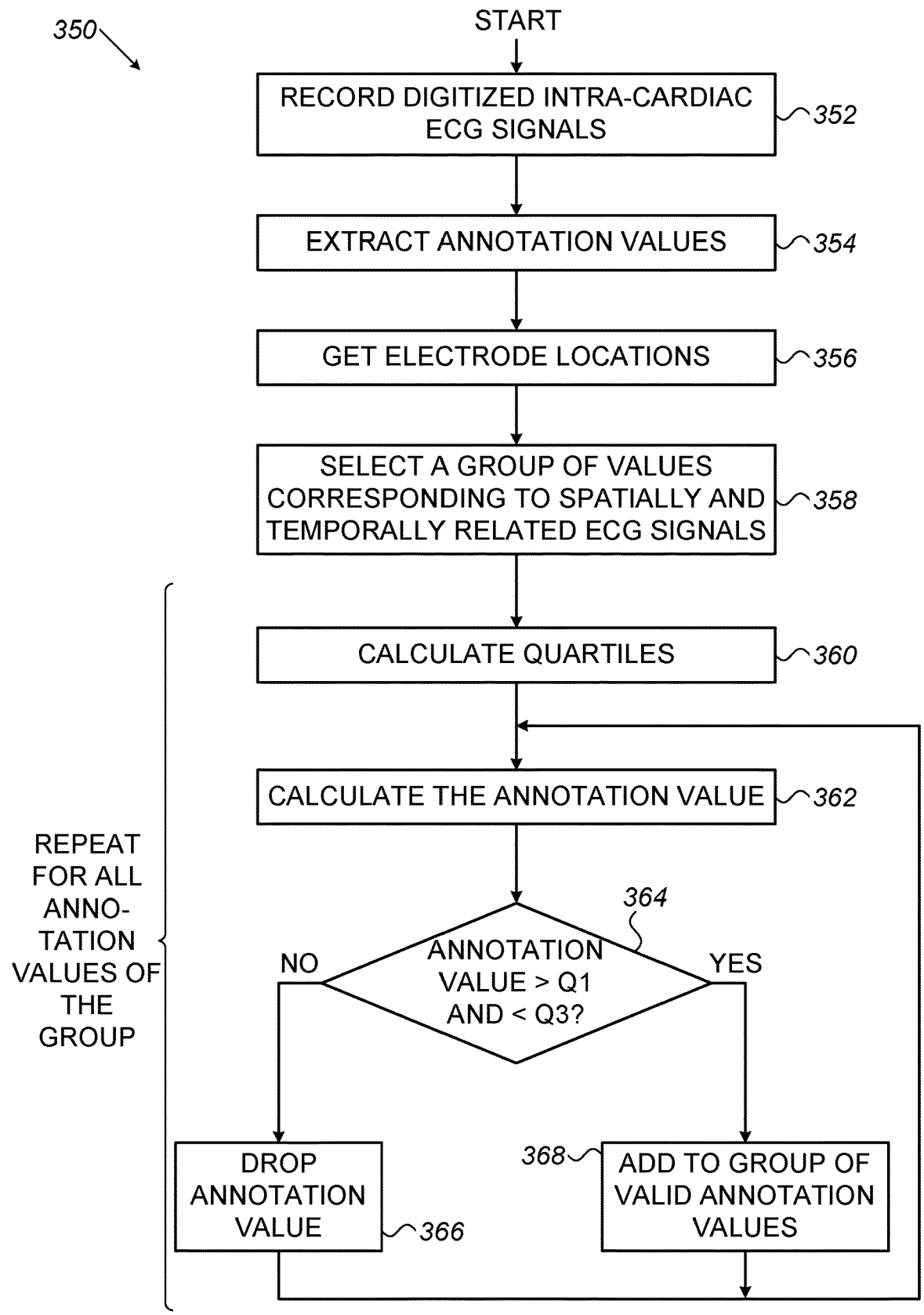
FIG. 3B is a flow chart that schematically illustrates a second method for enhancing the reliability of annotation values, in accordance with an embodiment of the present invention.

FIG. 3B is a flow chart 350 that schematically illustrates a second method for enhancing the reliability of annotation values, according to embodiments of the present invention. The method illustrated in FIG. 3B differs from the method illustrated in FIG. 3A only in the statistical characteristics and the selection of omitted values. Hence, steps 302 to 318 illustrated in FIG. 3A are identical, respectively, to steps 352 to 368 of FIG. 3B, except for steps 360 and 364, which are different from steps 310, 314 of FIG. 3A, and will be described hereinbelow.

In a Calculating Quartiles step 362, processing unit 42 (FIG. 1) calculates the first and the third quartiles (Q1 and Q3) of the group of LAT values (Q1 is defined as the middle number between the smallest number and the median of the group of LAT values; Q3 is the middle value between the median and the highest value of group of LAT values).

In a Comparing Annotation Value step 364, the processing units compares the annotated LAT value to Q1 and to Q3. If the value is smaller than Q1 or higher than Q3, the processing unit will enter Dropping Annotation Value step 366, wherein if the value is between Q1 and Q3, will enter Adding Value step 368.

The example flow charts shown in FIGS. 3A, 3B are chosen purely for the sake of conceptual clarity. In alternative embodiments, for example, annotation values may be extracted when the signal is acquired (rather than after the signal is recorded). In an embodiment, the selection of the signals of the group may be done by the physician; in other embodiments the processing unit will select the group, according to an area and/or a time range that the physician indicates.

In some embodiments, step 318 (368 in FIG. 3B) is not needed—the processing unit will, in step 316 (366), drop extreme values from the group, and when the flow is completed only the good values will remain. In other embodiments, all annotation values are initially marked as invalid, and step 316 (366) is not needed.

In some embodiments, other statistical characteristics that are used, different than those described above; for example, in an embodiment, octiles rather than quartiles may be used, and the processing unit may omit values lower than the first octile or higher than the last octile. Further alternatively, any other suitable percentile can be used.

Any other suitable statistical methods to detect and omit extreme values may be used in alternative embodiments.

Propagation Delay Compensation

In some embodiments, the technique described above may be improved by correcting the extracted LAT values, prior to statistical characteristics calculation, for expected changes in value due to different spatial positions of the electrodes. For example, the wave through the heart can be assumed to travel at a given speed (e.g., 1 m/s). Using the known positions of the electrodes acquiring the signals, theoretical differences in LAT can be applied when calculating the mean.

Figure 4:
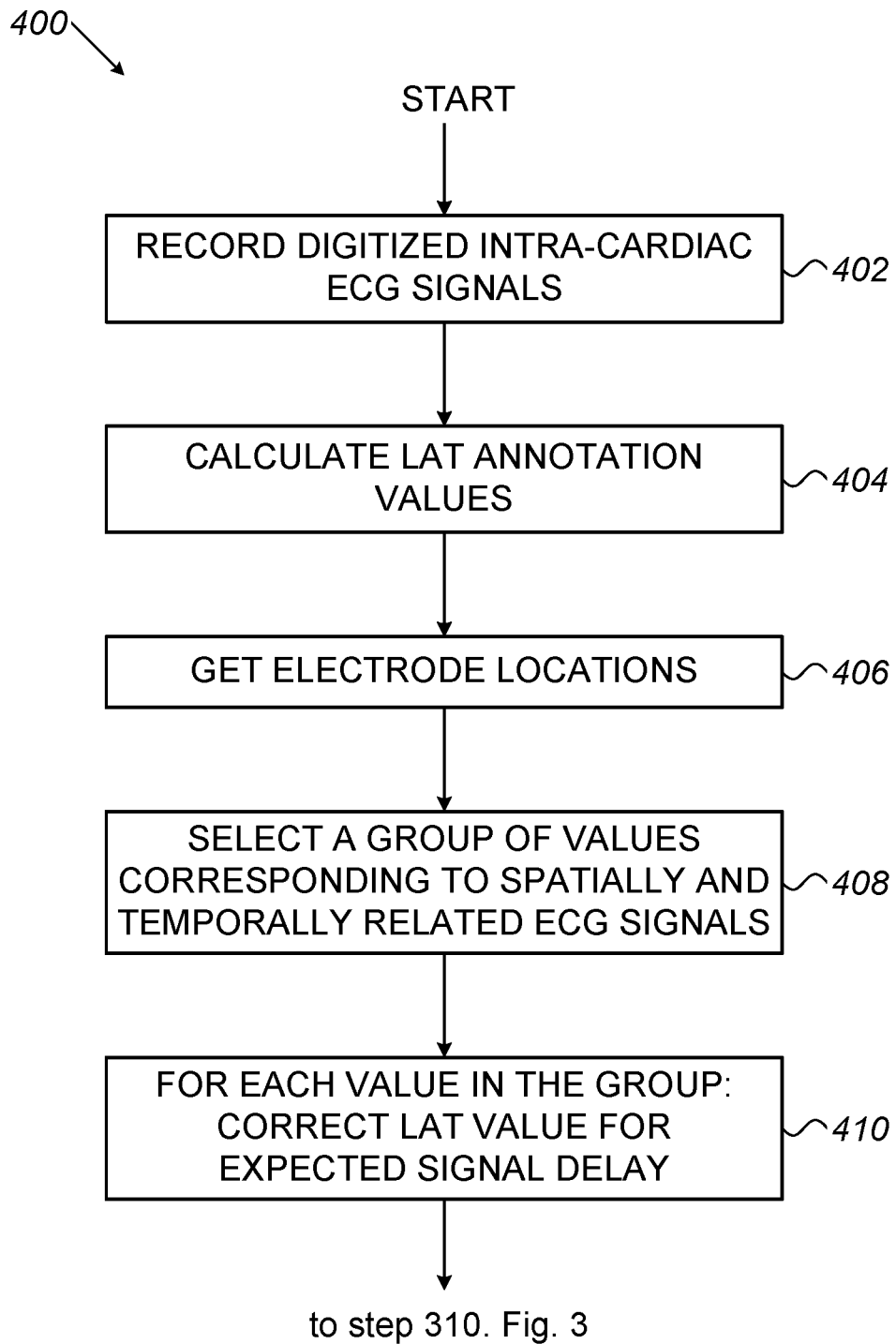
FIG. 4 is a flow chart that schematically illustrates an improved method for enhancing the reliability of annotation values, in accordance with an embodiment of the present invention.

FIG. 4 is a flow chart 400 that schematically illustrates an improved method for enhancing the reliability of annotation values, according to embodiments of the present invention. The flow is executed by processing unit 42 (FIG. 1). The flow starts at a Recording Signals step 402, followed by a Calculating Annotation Values step 404, a Getting Electrodes Location step 406 and a Selecting Group step 408, which may be identical, respectively, to steps 302, 304, 306 and 308 (FIG. 3).

Next, the processing unit enters a Correcting LAT Value step 410, wherein, for each LAT value of the group, the processing unit calculates and applies an estimated correction according to the spatial position of the electrode and the assumed wave travel speed. After step 410, the flow reverts to FIG. 3, at Calculating Mean and SD step 310.

Thus, an estimate of the deviation that is caused by propagation delay can be removed from the group, further enhancing the reliability of the annotation signals.

The example flow chart shown in FIG. 4 is chosen purely for the sake of conceptual clarity. In alternative embodiments, for example, the correction for anticipated signal delay can be integrated in the Calculating Mean and SD step. In other embodiments, the correction is done before the groups are selected (and, thus, groups may comprise a larger number of related LAT values).

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
signal acquisition circuitry, which is configured to receive multiple intra-cardiac signals acquired by multiple electrodes of an intra-cardiac probe in a heart of a patient; and
a processor, which is configured to:
  extract multiple annotation values from the intra-cardiac signals;
  select a group of the intra-cardiac signals;
  correct one or more of the annotation values in a given intra-cardiac signal, acquired by a given electrode in the group, to compensate for a displacement of the given electrode relative to the other electrodes in the group;
  identify in the group one or more annotation values that are statistically deviant in the group by more than a predefined measure of deviation; and
  visualize the annotation values to a user, excluding the statistically deviant annotation values;
wherein:
  the annotation values comprise local activation times;
  correcting one or more of the annotation values in the given intra-cardiac signal acquired by the given electrode in the group comprises:
    calculating a correction based on the spatial position of the given electrode and a wave travel speed; and
    removing deviation caused by propagation delay by applying the correction to the annotation value for the given electrode in the group;
  and
  visualizing the annotation values to the user comprises overlaying the annotation values on a model of the heart during a procedure in which the intra-cardiac signals were acquired.

2. The system according to claim 1, wherein the processor is configured to define the measure of the deviation in terms of a standard score of the annotation values.

3. The system according to claim 1, wherein the processor is configured to define the measure of the deviation in terms of one or more percentiles of the annotation values.

4. The system according to claim 1, wherein the processor is configured to calculate deviations of the annotation values over intra-cardiac signals acquired by a selected subset of spatially-related electrodes located no more than a predefined distance from one another in the heart.

5. The system according to claim 1 wherein, in calculating deviations of the annotation values, the processor is configured to average the intra-cardiac signals over multiple temporally-related cardiac cycles that occur within a predefined time duration.

* * * * *